United States Patent
Aoki (10) Patent No.: US 12,315,361 B2
(45) Date of Patent: May 27, 2025

(54) POSTURE CORRECTION SYSTEM, POSTURE CORRECTION METHOD, AND PROGRAM

(71) Applicant: TOYOTA JIDOSHA KABUSHIKI KAISHA, Toyota (JP)

(72) Inventor: Eisuke Aoki, Toyota (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 118 days.

(21) Appl. No.: 18/200,720

(22) Filed: May 23, 2023

(65) Prior Publication Data

US 2023/0419794 A1 Dec. 28, 2023

(30) Foreign Application Priority Data

Jun. 28, 2022 (JP) .................. 2022-103189

(51) Int. Cl.
*G08B 23/00* (2006.01)
*G08B 5/38* (2006.01)
*G08B 6/00* (2006.01)
*G08B 21/24* (2006.01)

(52) U.S. Cl.
CPC ................ *G08B 5/38* (2013.01); *G08B 6/00* (2013.01); *G08B 21/24* (2013.01)

(58) Field of Classification Search
CPC .. G08B 5/38; G08B 6/00; G08B 21/24; A61B 5/4561; A61B 5/1116; A61N 1/36; G16H 20/30
USPC ....................................................... 340/573.7
See application file for complete search history.

(56) References Cited

U.S. PATENT DOCUMENTS

| | | | |
|---|---|---|---|
| 2013/0179023 A1* | 7/2013 | Schmidt ............ | B60W 30/0956 701/23 |
| 2014/0167463 A1 | 6/2014 | Sakata et al. | |
| 2018/0003980 A1* | 1/2018 | Wilson ............... | G02B 27/0093 |
| 2018/0314065 A1* | 11/2018 | Li ....................... | G02B 27/0103 |

FOREIGN PATENT DOCUMENTS

| | | |
|---|---|---|
| JP | 2003-070768 A | 3/2003 |
| JP | 2005-267491 A | 9/2005 |
| JP | 2009-219508 A | 10/2009 |
| JP | 2014-118030 A | 6/2014 |
| JP | 2017-178131 A | 10/2017 |
| JP | 2019-129459 A | 8/2019 |
| JP | 2020-099550 A | 7/2020 |
| JP | 2022-092547 A | 6/2022 |

* cited by examiner

*Primary Examiner* — Tai T Nguyen
(74) *Attorney, Agent, or Firm* — Oliff PLC (57) ABSTRACT

To provide a posture correction system, a posture correction method, and a program each adapted to correct a posture of a user. A posture correction system includes directing means for directing a line of sight of a user to a position higher than a position of a gazing region which the user gazes at, thereby prompting the user to stretch his/her cervical and thoracic vertebrae.

6 Claims, 6 Drawing Sheets

POSTURE CORRECTION SYSTEM, POSTURE CORRECTION METHOD, AND PROGRAM

CROSS REFERENCE TO RELATED APPLICATIONS

This application is based upon and claims the benefit of priority from Japanese patent application No. 2022-103189, filed on Jun. 28, 2022, the disclosure of which is incorporated herein in its entirety by reference.

BACKGROUND

The present disclosure relates to a posture correction system, a posture correction method, and a program each adapted to correct a user's posture.

An apparatus for reducing strain on the eyes of a user by changing the relative height of a chair and a display, or by changing the height of a desk or a display is known (e.g. Japanese Unexamined Patent Application Publication No. 2005-267491).

SUMMARY

However, the aforementioned apparatus is not expected to be effective in correcting a user's posture. The present disclosure has been made in view of the problem mentioned above and a main aim of the present disclosure is to provide a posture correction system, a posture correction method, and a program each adapted to correct a posture of a user.

A first exemplary aspect for achieving the aforementioned aim is a posture correction system including directing means for directing a line of sight of a user to a position higher than a position of a gazing region which the user gazes at, thereby prompting the user to stretch his/her cervical and thoracic vertebrae.

According to the first exemplary aspect, an object for directing the line of sight of the user may be located at a position higher than the position of the gazing region, and the directing means may increase the visual stimulus from the object to the user so that it is greater than the visual stimulus from the gazing region to the user.

According to the first exemplary aspect, the directing means may increase the visual stimulus from the object to the user while reducing the visual stimulus from the gazing region to the user.

According to the first exemplary aspect, the gazing region may be a first display unit which the user gazes at, and a second display unit serving as the object may be located at a position higher than the position of the first display unit, and
the directing means may increase the visual stimulus from the second display unit to the user so that it is greater than the visual stimulus from the first display unit to the user.

According to the first exemplary aspect, the visual stimulus may be light, and
the directing means may form at least one of increasing the brightness of the light serving as the object for directing the line of sight of the user, flashing the light, changing the color of the light, and making the light serving as the object move.

According to the first exemplary aspect, the posture correction system further includes detecting means for detecting a height of the head of the user,
in which when it is determined that the height of the head of the user detected by the detecting means is equal to or below a threshold value, the directing means may direct the line of sight of the user to a position higher than the position of the gazing region, thereby prompting the user to stretch his/her cervical and thoracic vertebrae.

According to the first exemplary aspect, after directing the line of sight of the user to a position higher than the position of the gazing region, the directing means may increase the visual stimulus from the object to which the line of sight of the user is directed so that the user keeps the stretched state of his/her cervical vertebrae of the neck for a predetermined time or longer.

According to the first exemplary aspect, the user may be seated in a chair, and
the directing means may prompt the user to stretch his/her cervical and thoracic vertebrae by adjusting the relative positional relationship between the height of the object for directing the line of sight of the user and the chair so that the user faces upward.

According to the first exemplary aspect, the posture correction system further includes electrical stimulus generating means for providing electrical stimulus to the muscles used when the user stretches his/her cervical and thoracic vertebrae,
in which the directing means may direct the line of sight of the user to a position higher than a position of the gazing region which the user gazes at and also control the electrical stimulus generating means to provide electrical stimulus to the muscles used when the user stretches his/her cervical and thoracic vertebrae, thereby prompting the user to stretch his/her cervical and thoracic vertebrae.

A second exemplary aspect for achieving the aforementioned aim may be a posture correction method including directing a line of sight of a user to a position higher than a position of a gazing region which the user gazes at, thereby prompting the user to stretch his/her cervical and thoracic vertebrae.

A third exemplary aspect for achieving the aforementioned aim may be a program for causing a computer to execute the process of directing the line of sight of a user to a position higher than a position of a gazing region which the user gazes at, thereby prompting the user to stretch his/her cervical and thoracic vertebrae.

According to the present disclosure, it is possible to provide a posture correction system, a posture correction method, and a program each adapted to correct a posture of a user.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

First Embodiment

Figure 1:
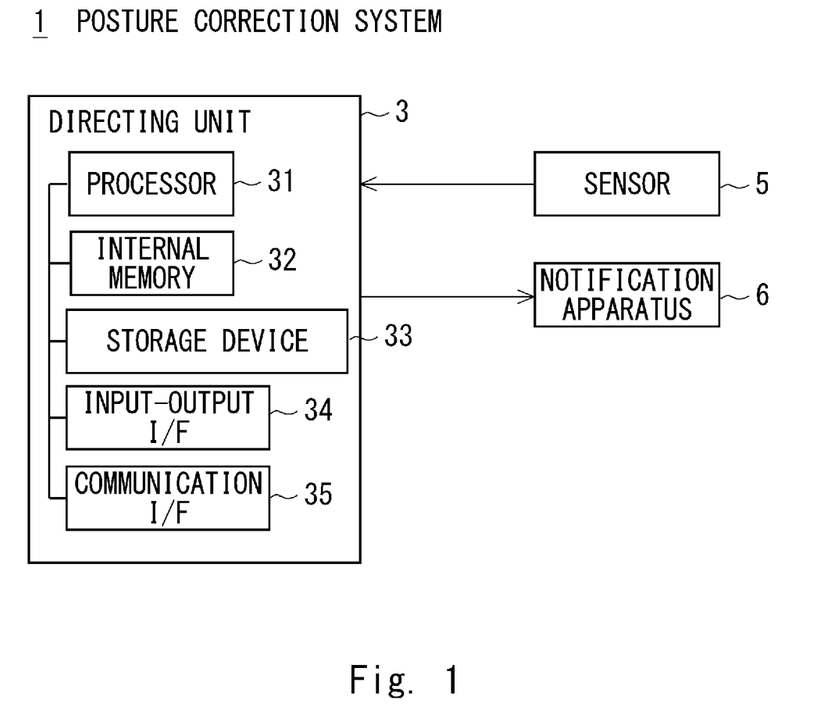
FIG. 1 is a block diagram showing a schematic configuration of a posture correction system according to an embodiment.

Hereinbelow, embodiments of the present disclosure will be described with reference to the drawings. FIG. 1 is a block diagram showing a schematic configuration of a posture correction system according to an embodiment. A posture correction system 1 according to the present embodiment is configured to correct a posture of a user, eliciting positive emotions, which will be described later.

It is said that positive emotions enhance the ability of a person to be happy. Earlier research has revealed that a good posture elicits positive emotions and a poor posture elicits negative emotions.

Figure 2:
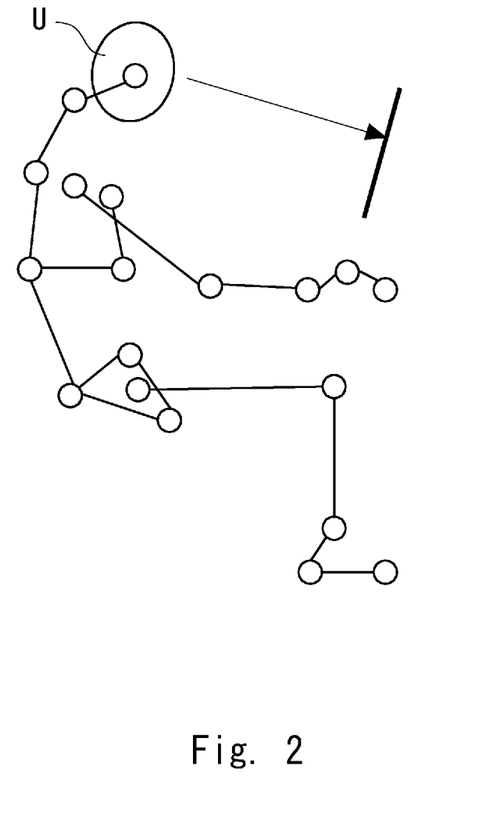
FIG. 2 is a diagram showing an example of a poor sitting posture.

For example, as shown in FIG. 2, an example of a poor sitting posture includes a leaning forward posture (i.e. a posture in which the head is bent forward). In the leaning forward posture, in which the head is positioned more forward than the torso, an extension moment strongly acts on the human body, resulting in excessive muscle tension in the head extensor and the trapezius muscles, which is a factor in causing disorders such as stiff shoulders. VDT (Visual Display Terminals) work involves gazing at a target object for a long time while keeping a sitting posture and keeping the line of sight fixed. In this case, the head is prone to be fixed in the forward direction. The anomalous position of the head is the starting point of an abnormal kinetic chain from the extremity of the body, causing changes in the spinal alignment, and the prolonged malalignment spreads throughout the whole body inducing compensation and compensatory movements. Such an anomalous position of the head is a factor in causing not only negative emotions but also physical disorders.

Figure 3:
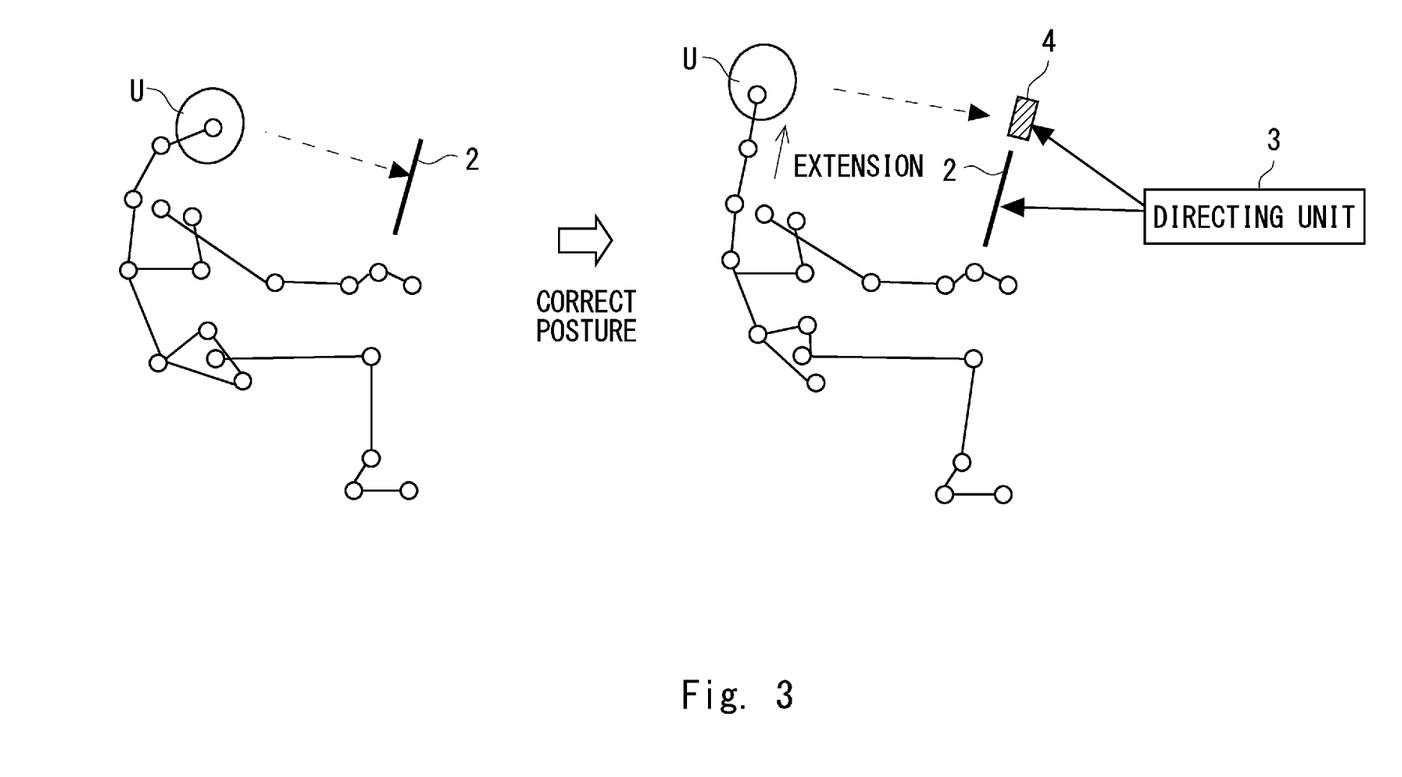
FIG. 3 is a diagram showing a configuration in which an object for directing the line of sight of a user is located at a position higher than the position of a display unit.

On the other hand, as shown in FIG. 3, the posture correction system 1 according to the present embodiment includes a directing unit 3 for directing the line of sight of the user U to a position higher than the position of a gazing region 2 which the user U gazes at, thereby prompting the user U to stretch his/her cervical and thoracic vertebrae.

By this configuration, it is possible to change the angle of the head of the user U sharply by having the user turn his/her face upward, and using the combined cervical extension exercise of his/her upper and lower cervical vertebrae as the starting point of the kinetic chain, the spinal alignment can be adjusted, thereby the posture of the user U is corrected. For example, when the line of sight of the user U is directed upward at a large angle, the neck of the user U tilts backward at a sharp angle. Then, in order to keep his/her balance, the user U sticks his/her chest out, straightens his/her back, and tilts his/her pelvis forward. This prompts the user U to stretch his/her cervical and thoracic vertebrae, whereby the sciatic bone of the user U is straightened, thereby enabling the user to have a good posture while sitting.

By correcting the posture, it is possible to, for example, reduce the risk of back pain and stiff shoulders of seated workers caused by poor posture. Further, since the user U automatically turns his/her face upward by having his/her line of sight directed as described above, the user U can be made to assume a correct posture without knowing it. And, when the user has his/her posture corrected, elicitation of positive emotions which enhance the ability of the user to be happy can be expected.

An example of the aforementioned gazing region 2 is a display screen of a display unit 2 at which the user U gazes while being seated. Examples of the display unit 2 include a crystal display or an organic EL (Electro Luminescence) display of a PC (Personal Computer).

The directing unit 3 is a specific example of directing means. As shown in, for example, FIG. 1, the directing unit 3 has a hardware configuration of a normal computer including a processor 31 such as a CPU (Central Processing Unit), a GPU (Graphics Processing Unit), or the like, an internal memory 32 such as a RAM (Random Access Memory), a ROM (Read Only Memory), or the like, a storage device 33 such as a HDD (Hard Disk Drive), a SSD (Solid State Drive), or the like, an input-output I/F 34 for connecting peripheral devices such as a display, and an input-output I/F 35 for performing communication with the external devices.

As shown in FIG. 3, an object 4 for drawing attention of the user U and directing the line of sight of the user U (hereinafter referred to as an object 4) may be located at a position higher than the position of the display unit 2. The directing unit 3 increases the visual stimulus from the object 4 to the user U so that it is greater than the visual stimulus from the display unit 2 to the user U. For example, when directing the line of sight of the user U, the directing unit 3 makes the brightness of the object 4 higher than the brightness of the display screen of the display unit 2 which is the gazing region 2, to thereby direct the line of sight of the user U.

Note that the directing unit 3 may direct the line of sight of the user U upward by first displaying the object 4 on the display screen of the display unit 2 to attract the line of sight of the user U, and then gradually moving the object 4 upward, until finally moving the object 4 to a position higher than the position of the display unit 2. In response to the visual stimulus from the object 4 located at the aforementioned high position, the user U turns his/her face in the upward direction towards the object 4, whereby it is possible to prompt the user U to stretch his/her cervical and thoracic vertebrae, thereby the posture of the user U is corrected.

The visual stimulus may be, for example, light. The directing unit 3 may perform at least one of increasing the brightness of the light serving as the object 4 for directing the line of sight of the user U, flashing the light, changing the color of the light, and making the light serving as the object 4 move. Making the light serving as the object 4 move refers to having a glowing character icon serving as the object 4 move, having a light serving as the object 4 move, and the like. By this configuration, it is possible to increase the visual stimulus from the object 4 to the user so that it is greater than the visual stimulus from the display unit 2 to the user U, and thus attract the line of sight of the user U to the object 4.

The directing unit 3 may, for example, control a projector or a pointer to project the object 4, such as an arbitrary figure or a character, on a screen or a wall that is located at a position higher than the position of the display unit 2. Further, the directing unit 3 may be located at a position higher than the position of the display unit 2, and may control a light apparatus serving as the object 4.

Note that a position located higher than the position of the display unit 2 is, for example, a position towards which the user U turns his/her face and faces upward, thereby prompting the user U to stretch his/her cervical and thoracic vertebrae. Such a position is determined experimentally, and can be set by the directing unit 3 in advance.

The directing unit 3 may increase the visual stimulus from the object 4 to the user U while reducing the visual stimulus from the display unit 2 to the user U which is the gazing region 2. For example, the directing unit 3 may make the brightness of the object 4 high while lowering the brightness of the display screen of the display unit 2 serving as the gazing region 2, or may turn off the power of the display unit 2 to darken the display screen. Note that the directing unit 3 may lower the visual stimulus from the display unit 2, which the gazing region 2, to the user U while maintaining the visual stimulus from the object 4 to the user U as it is.

This enhances the visual stimulus from the object 4 located at the aforementioned high position, making the user U more prone to turn his/her face in the upward direction towards the object 4, whereby it is possible to more effectively prompt the user U to stretch his/her cervical and thoracic vertebrae, thereby the posture of the user U is corrected.

Further, the directing unit 3 may increase the visual stimulus from the object 4 to the user U while outputting a sound from a speaker or the like located at a position higher than the position of the display unit 2. By this configuration, in response to the visual stimulus from the object 4 located at the aforementioned high position and the output sound, the user U is more prone to turn his/her face in the upward direction towards the object 4, whereby it is possible to more effectively prompt the user U to stretch his/her cervical and thoracic vertebrae, thereby the posture of the user U is corrected.

Figure 4:
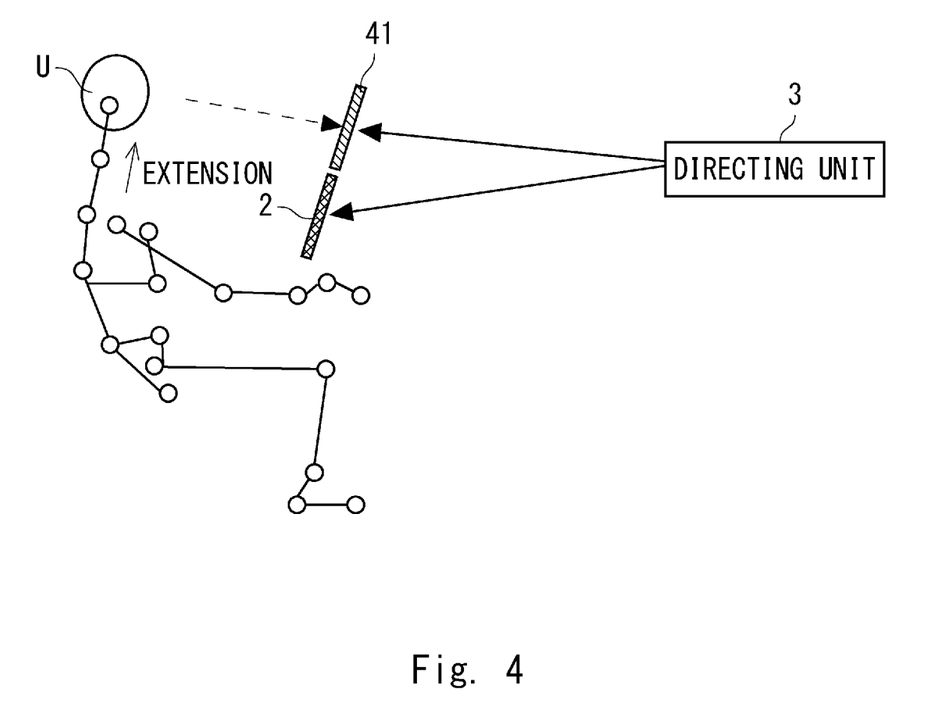
FIG. 4 is a diagram showing a configuration in which a second display unit is located at a position higher than the position of a first display unit.

As shown in FIG. 4, the gazing region 2 is a first display unit 2 which the user U gazes at, and a second display unit 41 serving as the object 4 may be located at a position higher than the position of the first display unit 2. The directing unit 3 increase the visual stimulus from the second display unit 41 to the user U so that it is greater than the visual stimulus from the first display unit 2 to the user U. For example, the directing unit 3 makes the brightness of the display screen of the second display unit 41 higher than the brightness of the display screen of the first display unit 2. In response to the visual stimulus from the second display unit 41 located at the aforementioned high position, the user U turns his/her face in the upward direction towards the second display unit 41 whereby it is possible to prompt the user U to stretch his/her cervical and thoracic vertebrae, thereby the posture of the user U is corrected. Note that at this time, the first display unit 2 and the second display unit 41 may display the same screen. By this configuration, it is possible for the user to continue to look at the same display content while having the user's posture corrected.

The directing unit 3 may, for example, increase the visual stimulus from the object 4 to the user U so that it is greater than the visual stimulus from the display unit 2 to the user U within a set predetermined cycle or a predetermined time. By this configuration, it is possible to prompt the user U to stretch his/her cervical and thoracic vertebrae within the set predetermined cycle or the predetermined time, thereby the posture of the user U is corrected.

When it is determined that the height of the head of the user U detected by a sensor 5 such as a camera is equal to or below the threshold value, the directing unit 3 may direct the line of sight of the user U to a position higher than the position of the display unit 2, thereby prompting the user U to stretch his/her cervical and thoracic vertebrae (FIG. 1).

The sensor 5 is a specific example of detecting means. By this configuration, it is possible to automatically detect whether or not the height of the head of the user U is equal to or below a threshold value and the posture of the user U is in a poor state, whereby prompting the user U to stretch his/her cervical and thoracic vertebrae, thereby the posture of the user U is corrected.

When it is determined that the height of the head of the user U detected by the sensor 5 such as a camera is equal to or below the threshold value, the directing unit 3 may direct the line of sight of the user U to a position higher than the position of the display unit 2 and also notify the user U, using a notification apparatus 6, that he/she is sitting in a poor posture.

The notification apparatus 6 may perform notification by, for example, changing the brightness of the display unit 2, turning off the power of the display unit 2, displaying the height of the head of the user U, or outputting sound or vibration. By this configuration, it is possible to not only direct the line of sight of the user U but also to make the user U be aware that he/she is sitting in a poor posture with his/her head down and to remind the user U to stretch his/her head in the upward direction more frequently.

After directing the line of sight of the user U to a position higher than the position of the display unit 2, the directing unit 3 may increase the visual stimulus from the object 4 to which the line of sight of the user U is directed so that the user U keeps the stretched state of the cervical vertebrae of his/her neck for a predetermined time or longer. For example, the directing unit 3 may increase the brightness of the object 4 so that the user U keeps the stretched state of the cervical vertebrae of his/her neck for a predetermined time or longer. By this configuration, the posture of the user can be corrected more effectively since the user U keeps the stretched state of his/her cervical and thoracic vertebrae for a predetermined time or longer.

Next, a posture correction method according to an embodiment will be described. In the posture correction method according to the present embodiment, the line of sight of the user U is directed to a position higher than the position of the display unit 2 which the user U gazes at, thereby prompting the user U to stretch his/her cervical and thoracic vertebrae. By this configuration, it is possible to change the angle of the head of the user U largely by having the user turn his/her face upward, and using the combined cervical extension exercise of his/her upper and lower cervical vertebrae as the starting point of the kinetic chain, the spinal alignment can be adjusted, thereby the posture of the user U can be corrected.

Second Embodiment

Figure 5:
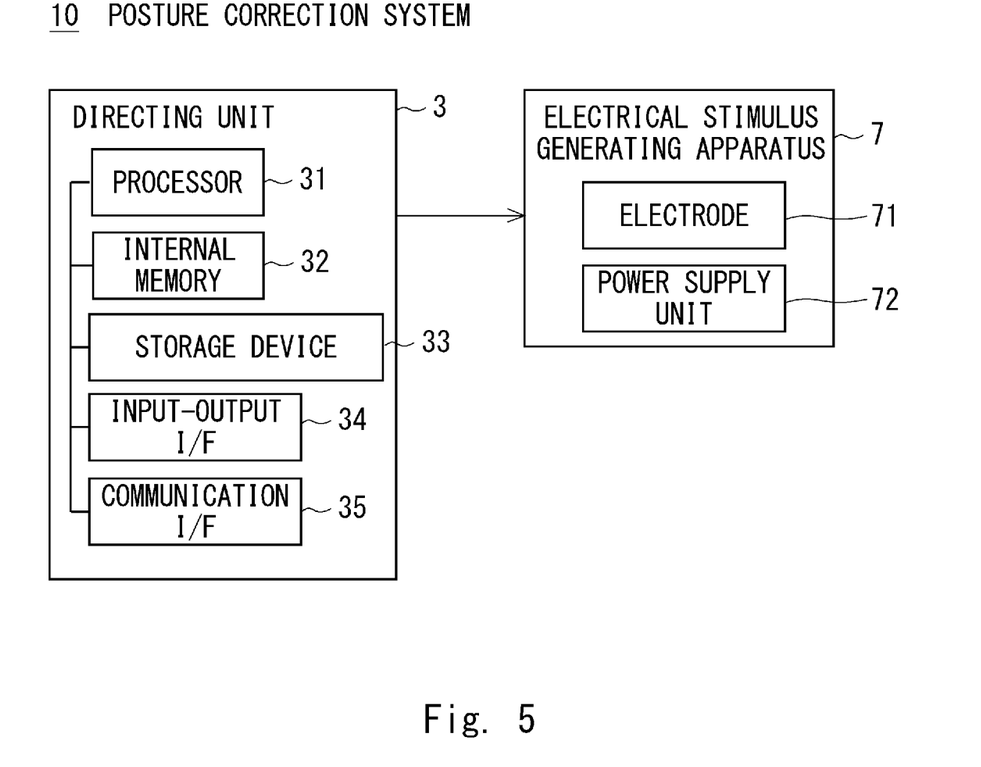
FIG. 5 is a block diagram showing a schematic configuration of a posture correction system according to an embodiment.

FIG. 5 is a block diagram showing a schematic configuration of a posture correction system according to an embodiment. The posture correction system 10 according to the present embodiment further includes an electrical stimulus generating apparatus 7 that provides electrical stimulus to the muscles used when the user U stretches his/her cervical and thoracic vertebrae.

The electrical stimulus generating apparatus 7 is a specific example of electrical stimulus means. The electrical stimulus generating apparatus 7 includes an electrode 71 to be attached to the muscle part of the user U used for assisting extension exercise of the user's cervical and thoracic vertebrae and a power supply unit 72 for supplying power to the electrode 71.

The electrical stimulus generating apparatus 7 supplies power to the electrode 71 attached to the muscle part of the user U and provides electrical stimulus to tense the muscles of the user U so as to stimulate extension exercise of the user U's cervical and thoracic vertebrae.

The directing unit 3 directs the line of sight of the user U to a position higher than the position of the display unit 2 which the user U gazes at and also controls the electrical stimulus generating apparatus 7 to provide electric al stimulus to the muscles used when the user U stretches his/her cervical and thoracic vertebrae, thereby prompting the user U to stretch his/her cervical and thoracic vertebrae.

For example, the directing unit 3 makes the brightness of the second display unit 41 that is located at a position higher than the position of the first display unit 2 serving as the gazing region 2 higher and also controls the electrical stimulus generating apparatus 7 to provide electrical stimulus to the muscles used when the user U stretches his/her cervical and thoracic vertebrae, thereby prompting the user U to stretch his/her cervical and thoracic vertebrae.

By this configuration, in response to the visual stimulus and the electrical stimulus from the object 4 located at the aforementioned high position, the user U is more prone to turn his/her face to the object 4 located in the upward direction, whereby it is possible to more effectively prompt the user U to stretch his/her cervical and thoracic vertebrae, thereby the posture of the user U is corrected.

The directing unit 3 may provide, using the electrical stimulus generating apparatus 7, electrical stimulus to the muscles that are used when the user U stretches his/her cervical and thoracic vertebrae, whereby the user U is prompted to stretch his/her cervical and thoracic vertebrae, thereby the posture of the user U is corrected.

Third Embodiment

Figure 6:
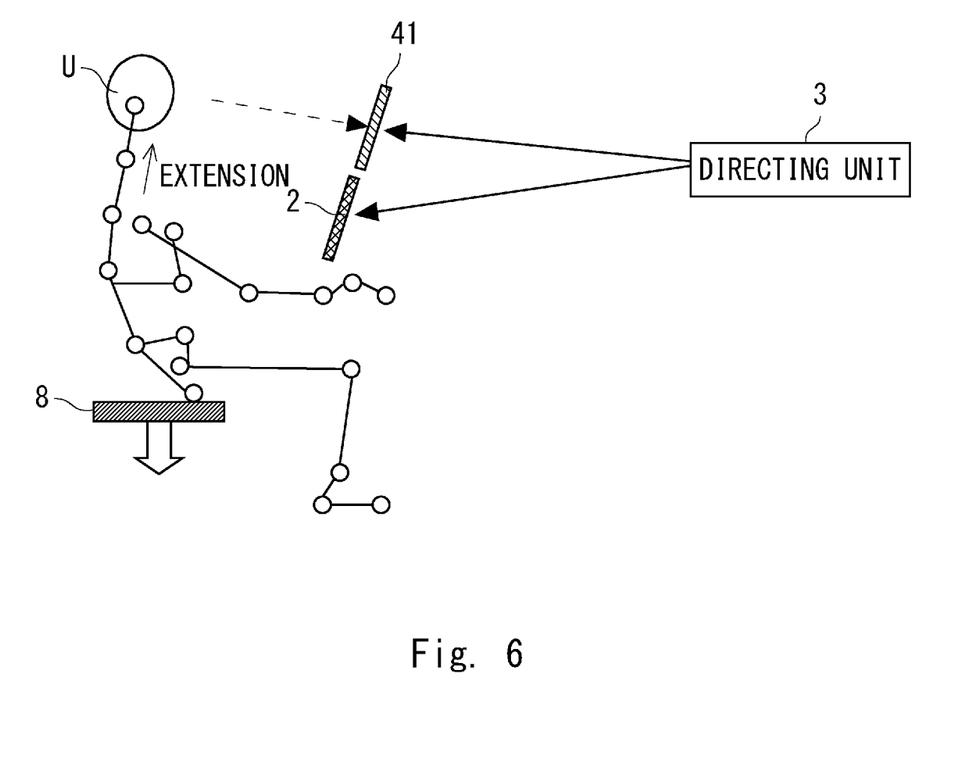
FIG. 6 is a diagram showing a configuration in which a seat surface of a chair is lowered while an object for directing the line of sight of a user is located at a position higher than the position of the display unit.

In the present embodiment, the directing unit 3 prompts the user U to stretch his/her cervical and thoracic vertebrae by adjusting the relative positional relationship between the height of the object 4 for directing the line of sight of the user U and the chair the user U is sitting so that the user U turns his/her face in the upward direction.

For example, the directing unit 3 lowers the seat surface of the chair while keeping the height of the object 4 for directing the line of sight of the user U to be at the height of the display unit 2. Alternatively, the directing unit 3 may lower the height the surface of chair the user U is sitting while maintaining the height of the display unit 2 which the user U gazes at. By this configuration, since the head of the user U is lowered with respect to the object 4 or the display unit 2 by the amount the seat surface of the chair is lowered, the user U naturally looks up towards the object 4 or the display unit 2, whereby it is possible to prompt the user U to stretch his/her cervical and thoracic vertebrae, thereby the posture of the user U is corrected.

Note that as shown in FIG. 6, the directing unit 3 may lower the seat surface 8 of the chair the user U is sitting while having the object 4 for directing the line of sight of the user U located at a position higher than the position of the display unit 2. By this configuration, the user U looks up towards the object 4 at an acute angle, whereby it is possible to effectively prompt the user U to stretch his/her cervical and thoracic vertebrae, thereby the posture of the user U can be corrected.

Further, the directing unit 3 may prompt the user U to stretch his/her cervical and thoracic vertebrae by bringing a predetermined object that causes discomfort to the user U located in the line of sight of the user U relatively close to the user U. By bringing a predetermined object that generates discomfort to the user U located in the line of sight of the user U relatively close to the user U, the user U unconsciously pulls his/her body back and tries to keep a distance from the object. In doing so, the user U draws his/her chin back and stretches his/her chest, whereby the user U is prompted to stretch his/her cervical and thoracic vertebrae, thereby the posture of the user U can be corrected.

While the embodiments of the present disclosure have been described, they are mere examples and the scope of the present disclosure is not to be limited to these embodiments. These embodiments can be implemented in any other forms, and can be omitted, replaced, changes in any way without departing from the gist of the present disclosure. These embodiments and modified examples thereof are included within the scope and the gist of the present disclosure, and are included in the invention described in the claims of the present disclosure and the equivalents thereof.

The present disclosure can be realized by, for example, having a processor execute a computer program for processing performed by the directing unit 3.

The program includes instructions (or software codes) that, when loaded into a computer, cause the computer to perform one or more of the functions described in the embodiments. The program may be stored in a non-transitory computer readable medium or a tangible storage medium. By way of example, and not a limitation, non-transitory computer readable media or tangible storage media can include a random-access memory (RAM), a read-only memory (ROM), a flash memory, a solid-state drive (SSD) or other types of memory technologies, a CD-ROM, a digital versatile disc (DVD), a Blu-ray disc or other types of optical disc storage, and magnetic cassettes, magnetic tape, magnetic disk storage or other types of magnetic storage devices.

The program may be transmitted on any type of transitory computer readable medium. By way of example, and not a limitation, transitory computer readable media or communication media can include electrical, optical, acoustical, or other forms of propagated signals. A transitory computer readable medium can provide the program to a computer via a wired communication line such as electric wires and optical fibers, or a wireless communication line.

The structural elements of the posture correction systems 1 and 10 described in the aforementioned embodiments cannot only be realized by the program but can also be realized by exclusive hardware such as ASIC (Application Specific Integrated Circuit) and FPGA (Field-Programmable Gate Array).

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A posture correction system comprising a processor and memory configured to direct a line of sight of a user to a position higher than a position of a gazing region which the user gazes at, thereby prompting the user to stretch his/her cervical and thoracic vertebrae, wherein the gazing region being a first display which the user gazes at, and a second display located at a position higher than the position of the first display, the processor is programmed to increase the visual stimulus from the second display to the user so that it is greater than the visual stimulus from the first display to the user, the visual stimulus is light, and the processor is programmed to perform at least one of increasing a brightness of the light serving as an object for directing the line of sigh of the user, flashing the light, changing a color of the light, and making the light serving as the object move.

2. The posture correction system according to claim 1, further comprising sensor configured to detect a height of a head of the user, wherein when it is determined that the height of the head of the user detected by the sensor is equal to or below a threshold value, the processor is programmed to direct the line of sight of the user to a position higher than the position of the gazing region, thereby prompting the user to stretch his/her cervical and thoracic vertebrae.

3. The posture correction system according to claim 1, wherein after directing the line of sight of the user to a position higher than the position of the gazing region, the processor is programmed to increase the visual stimulus from the object to which the line of sight of the user is directed so that the user keeps the stretched state of his/her cervical vertebrae of the neck for a predetermined time or longer.

4. The posture correction system according to claim 1, wherein the user is seated in a chair, and the processor is programmed to prompt the user to stretch his/her cervical and thoracic vertebrae by adjusting a relative positional relationship between a height of an object for directing the line of sight of the user and the chair so that the user faces upward.

5. The posture correction system according to claim 1, further comprising electrode configured to provide electrical stimulus to muscles used when the user stretches his/her cervical and thoracic vertebrae, wherein the processor is programmed to direct the line of sight of the user to a position higher than a position of the gazing region which the user gazes at and also controls the electrode to provide electrical stimulus to the muscles used when the user stretches his/her cervical and thoracic vertebrae, thereby prompting the user to stretch his/her cervical and thoracic vertebrae.

6. A posture correction system comprising directing a line of sight of a user to a position higher than a position of a gazing region which the user gazes at, thereby prompting the user to stretch his/her cervical and thoracic vertebrae, wherein the gazing region being a first display which the user gazes at, and a second display is located at a position higher than the position of the first display, the processor is programmed to increase the visual stimulus from the second display to the user so that it is greater than the visual stimulus from the first display to the user, the visual stimulus is light, and the processor is programmed to perform at least one of increasing a brightness of the light serving as an object for directing the line of sigh of the user, flashing the light, changing a color of the light, and making the light serving as the object move.

* * * * *